United States Patent [19]

Nashner

[11] Patent Number: 4,738,269

[45] Date of Patent: Apr. 19, 1988

[54] APPARATUS AND METHOD FOR SENSORY INTEGRATION AND MUSCULAR COORDINATION ANALYSIS

[76] Inventor: Lewis M. Nashner, 3535 NE. Simpson St., Portland, Oreg. 97211

[21] Appl. No.: 873,125

[22] Filed: Jun. 11, 1986

Related U.S. Application Data

[63] Continuation of Ser. No. 408,184, Aug. 16, 1982, abandoned.

[51] Int. Cl.$^4$ .............................................. A61B 5/10
[52] U.S. Cl. .................................. 128/782; 272/146; 434/258
[58] Field of Search ................. 128/774, 779, 782; 272/144, 146; 434/55, 51, 247, 258

[56] References Cited

U.S. PATENT DOCUMENTS

| 2,670,729 | 3/1954 | Grant | 128/782 |
| 3,859,736 | 1/1975 | Hill et al. | 434/55 |
| 3,890,722 | 6/1975 | Nuner | 434/55 |
| 3,906,931 | 9/1975 | Tereklov | 128/782 |
| 4,164,080 | 8/1979 | Kosydar et al. | 434/55 |

FOREIGN PATENT DOCUMENTS

| 695656 | 11/1979 | U.S.S.R. | 128/782 |
| 820803 | 4/1981 | U.S.S.R. | 128/782 |
| 904663 | 2/1982 | U.S.S.R. | 128/782 |

OTHER PUBLICATIONS

Nashner, L. M. and A. Berthoz., *Visual Contribution to Rapid Motor Responses During Postural Control*, Brain Research, 150:403–407, 1978.
Nashner, L. M., M. Woollacott and G. Tuma, *Organization of Rapid Responses to Postural and Locomotor-Like Perturbations of Standing Man*, Exp. Brain Res., 36, 463–476, 1979.
Nashner, L. M., *Fixed Patterns of Rapid Postural Responses Among Leg Muscles During Stance*, Exp. Brain Res. 30, 13–24, (1977).
Nashner, L. M. and P. Wolfson., *Influence of Head Position and Proprioceptive Cues on Short Latency Postural Reflexes Evoked by Galvanic Stimulation of the Human Labyrinth*, Brain Research, 67, pp. 255–268, 1974.

Primary Examiner—William E. Kamm
Assistant Examiner—John C. Hanley
Attorney, Agent, or Firm—Bromberg, Sunstein & Casselman

[57] ABSTRACT

A subject's ability to maintain a position in equilibrium by organizing sensory orientation inputs is tested utilizing a support surface and a visual surround. These items are moved by servo control in relation to a subject's sway to provide perceptually misleading sensory orientation inputs to the subject, as part of various testing protocols.

18 Claims, 7 Drawing Sheets

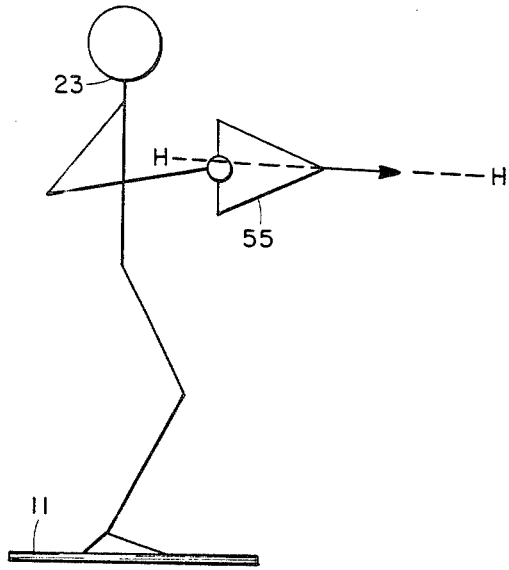
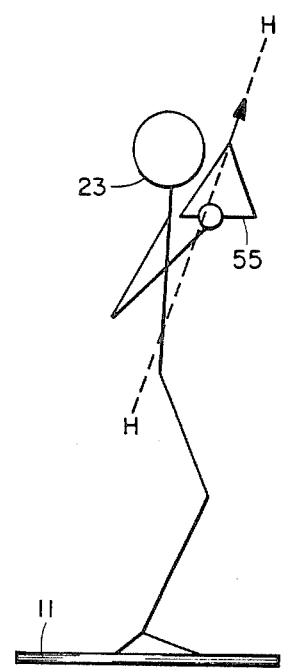
Fig. 6A  Fig. 6B
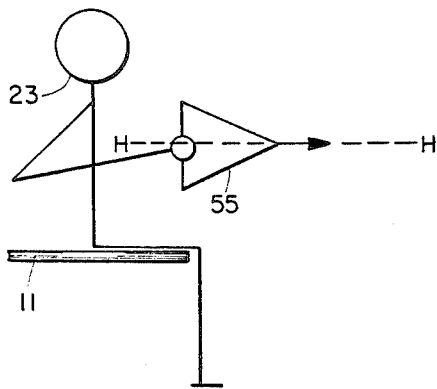
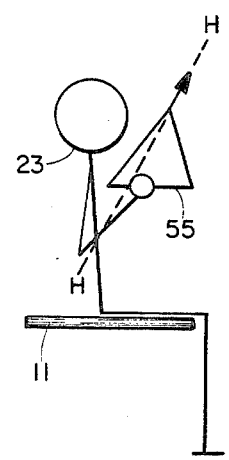
Fig. 6C  Fig. 6D

APPARATUS AND METHOD FOR SENSORY INTEGRATION AND MUSCULAR COORDINATION ANALYSIS

This is a continuation of co-pending application Ser. No. 408,184 filed on Aug. 16, 1982, now abandoned.

DESCRIPTION

1. Technical Field

This invention relates generally to methods and devices for measuring the existence and extent of a subject's ability to organize sensory orientation information and to coordinate muscular contractions required to correct or make shifts in position.

2. Background Art

It has long been a technique for diagnosing various neuromuscular disorders and other medical conditions to observe closely the physical comportment of a patient. Initially such observation amounted to little more than visually observing the physical posture or stability of the subject standing in various fixed freestanding positions, or his ability to perform simple motions or exert a certain force with a particular muscle. In recent times the visually observed sway of a standing individual has been one diagnostic technique. More recently such sway has been measured using a fixed strain-gauge forceplate, and by various photometric techniques.

The following chronology sumarizes developments.

1. First published reports of posture control applications to neurological disorders [Romberg, M. H. A manual of the Nervous Diseases of Man (E. H. Siereking, editor and translator) Sydenham Society, London (1853)]. Romberg visually observed the stability of subjects standing in various fixed freestanding postures.

2. First published reports using a fixed position strain-gauge forceplate to quantify the postural sway of a standing subject, so called "stabilometry" or "posturography", were in 1968 (Bensil, E. K., and Dzendalet, E. Power spectral density analysis of the standing sway of males, Perception and Psychophysics, 4: 285–288 (1968). Since that time, at least ten groups of investigators have used fixed forceplates to measure the sway motions of standing subjects.

3. The first published reports using a moving forceplate to perturb the equilibrium of a standing subject and measure the subsequent corrections was reported by applicant in 1970 (Nashner, L. M., *Sensory Feedback in Human Posture Control*, Massachusetts Institute of Technology, Report MVT-70-3, 1970). This article reported a platform that could independently translate in the horizontal anteroposterior direction and rotate about an axis colinear with the subject's ankle joints. This article also reported the experimental technique of rotating the platform in direct relation to the measured AP sway orientation angle of the subject. Since that time, several other groups have adapted use of a movable platform to analyze posture control in humans (Gurfinkel, V. S., Lipshits, M. I., Popov, K. Ye.) Is the stretch reflex the main mechanism in the system of regulation of the vertical posture in man? Biophysics 19: 744–748 (1974). Booth, J. B. and Stockwell, C. W. A method for evaluating vestibular control of posture, Oto-rhinolaryngology 86: 93–96 (1977). Other groups known to be using movable platforms are Dichgans, J., Mauritz, K. H., Dietz, V. at the Abteilung Klinische Neurologie and Neurophysiologie, Albert-Ludwigs-Universtat, Freiburg, West Germany.

Appendix B of Nashner, L. M., *Sensory Feedback in Human Posture Control*, Massachusetts Insitute of Technology, Report MVT-70-3, 1970, sets forth the following background art to the present invention, including a description of construction details of a means for measuring postural responses and causing functionally related rotation of a support surface that can be used in combination with the other elements set forth herein:

THE TWO-DEGREE OF FREEDOM EXPERIMENTAL PLATFORM

The platform provides the base on which the subject stands during experiments. It enables the experimenter to influence the control strategy of the subject and permits him to probe the states of the postural control system with small transient disturbances.

The platform performs two basic functions:

1. It measures ankle reaction torques and the body lean angle.

2. It introduces rotational and backwards and forward translational inputs to the ankle joints.

B.1. Measurement of Postural Responses

B.1.1 Ankle Torque Measurement

The plate on which the subject stands is supported at each of its four corners by a miniature variable resistance force transducer, (Clark Electronics, Micro-ducer No. CS-5-100L). Resistance bridges measure differential loading between front and back sensors on each side of the force plate. Differential load readings are amplified and summed, forming the next reaction torque reading. FIG. 10 shows the configuration.

Each force transducer is calibrated separately and resistance ranges are matched for each of the differential force bridges. Passive resistors in each bridge are set to balance the bridge at the nominal load of 70 pounds on each differential pair (one half the weight of an average subject).

The complete force plate is calibrated using large weights simulating the nominal load of 140 pounds.

FIG. 11 shows the static output characteristics of the force plate transducers as a function of net reaction torque. Linearity is within ±2.5% at full scale. Hysteresis errors during a given cycle are within ±5% of the maximum amplitude of the cycle.

The rated frequency response of each sensor is above 1000 hz, far better than necessary to measure postural responses.

B.1.2 Body Angle Measurement

Body angle is measured by the simple, 2-potentiometer and cable system, shown in FIG. 12. Two potentiometers, one on each hip, remove effects of vertical axis rotations. Sensitivity of the system is ±0.01 degrees.

B.2 Platform Motion Effectors

The force plate is maintained on a member which is able to rotate about an axis colinear to that of the ankle joint. A hydraulic ram and servo valve control the angle of the force plate member.

The entire supporting base rides on two roller bearings, allowing forward and backward motion of the platform. This motion is controlled by a secod hydraulic ram and valve system. The system is shown, schematically in FIG. 13.

The rotational servo loop consists of the following components:

1. proportional servo valve; Moog Model M-7700 @ 2700 psi; excitation push-pull.

2. 2-way hydraulic ram: 1¼ bore, 8" stroke.

3. rack and pinion potentiometer position feedback. Flow rates within the control valve limit the performance of the system. The transfer function shown in FIG. 14 describes closed loop platform rotational motion for amplitudes below ±2°. Frequency response is well above that required during experiments. The step response time, about 50 milliseconds, is adequate to observe a well defined reflex response.

The lateral position control loop operates open loop. Deflection velocity is controlled by a needle valve and monitored with rack and pinion potentiometer position feedback. Total deflection is fixed with adjustable restraining rings mounted on the hydraulic ram. An on-off relay valve controls activation of the lateral deflection loop.

Components are as follows:
1. relay valve, 2-way
2. double acting hydraulic cylinder, $\frac{7}{8}''$ bore, 4" stroke, adjustable with inserts from $\frac{1}{2}$ to 4"
3. rack and pinion actuated potentiometer for monitoring of lateral position.

Maximum deflection velocity is greater than 5 inches per second. Response (not including response time delary of the relay valve) is approximately first order with a response time of 10 milliseconds.

4. First published reports using platform displacements to analyze the temporal and spatial organization of muscular contractions (Nashner, L. M. Fixed patterns of rapid postural responses among muscles during stance, Exp Brain Res 30: 13–24, 1977).

5. First published reports using rotation of the visual surround about an axis colinear with the ankle joints and in the direct proportion to the measured anteroposterior sway orientation angle of the subject was made in: Nashner, L. M. and Berthoz, Visual contribution to rapid motor responses during posture control, Brain Res 150: 403–407, 1978).

The foregoing approaches, while important in furthering basic medical research, have not provided a systematic clinical tool for readily evaluating and identifying pathological conditions in a subject's ability to organize sensory orientation information and to coordinate muscular contractions. In particular, although significant data have been collected relating to a subject's competence in maintaining balance, there has been no clinical method for identifying systematically the cause or extent of a subject's lack of such competence. Typically causes are subtle and interactive, such that, for example, a subject's vestibular deficits may be masked by the subject's ability to compensate in utilizing other sensory inputs. Moreover it may be difficult to ascertain whether a subject's problems in maintaining balance are attributable to lack of appropriate sensory orientation information or alternatively to inability to coordinate muscles in response to appropriate information.

DISCLOSURE OF INVENTION

The present invention provides a method and device for measuring the existence and extent of a subject's ability to organize sensory orientation information and to coordinate contractions required to correct or make shifts in position. By masking sensory orientation information derived from visual and tactile inputs, the invention permits ready and separate identification and quantification of abnormalities attributable to a subject's inability to integrate or to obtain each of vestibular, tactile, and visual information. Moreover the invention permits separate identification and quantification of abnormalities attributable to a subject's inability to coordinate muscular responses.

In a preferred embodiment of a method in accordance with the invention, a subject is placed on a movable support surface, and the subject assumes a position of equilibrium. The subject's field of view is substantially surrounded with what I call a "visual surround." The subject's displacement from equilibrium is measured on a continuous or periodic basis, and the support surface and/or visual surround are moved in functional relaton to the measured displacement. Also the contractile activity of some or all of the subject's supporting musculature is measured as the subject attempts to maintain equilibrium. In a further specific embodiment based on this embodiment, the subject stands on the support surface, and the visual surround and support surface are moved about a common axis colinear with the subject's ankle joints, and the displacement measured is the anteroposterior sway of the subject.

In a preferred embodiment of the device in accordance with the present invention, there are provided a support surface and visual surround as discussed above, together with a measuring system for measuring, on a continuous or periodic basis, the subject's displacement from equilibrium, and a provision for moving each of the visual surround and the support surface in functional relation to the measured displacement. In a further specific embodiment of the device based on this embodiment, the visual surround and support surface are moved about a common axis that may be made collinear with the ankle joints of a subject standing on the support surface and the measuring system measures the anteroposterior sway of the subject.

BRIEF DESCRIPTION OF THE DRAWINGS

These and other features of the invention will be more readily understood by consideration of the following detailed description taken with the accompanying drawings, in which:

FIG. 5 shows the lateral sway displacement angle. FIG. 5A also shows the corresponding lateral sway displacement angle.

FIGS. 6A-6D show the use of a manipulandum in accordance with an embodiment of the invention, with the manipulandum positioned at the front or side of a subject standing or seated on the support surface.

FIG. 8 further shows the corresponding ankle torques and measure anteroposterior sway angles.

FIG. 9 further shows a reversal of temporal sequence of the responses of gastronemics and hamstring muscles of the subject's spastic leg, and shows an abnormal response amplitude ratio for pairs of muscles in the spastic leg.

FIG. 10 shows a schematic diagram of circuitry for use with a movable support surface (background art).

FIG. 11 shows the static output characteristics of the force plate transducers of FIG. 11 as a function of net reaction torque (background art).

FIG. 12A shows a side view, and FIG. 12B shows a top view, of a simple, 2-potentiometer and cable system for measuring body angle of a subject standing on the movable support surface of FIG. 10 (background art).

FIG. 13 shows a platform motion effector for use with the movable support surface of FIG. 10 (background art).

FIG. 14 shows a transfer function that described closed loop rotational motion for the movable support surface of FIG. 10 (background art).

DESCRIPTION OF SPECIFIC EMBODIMENTS

Figure 1:
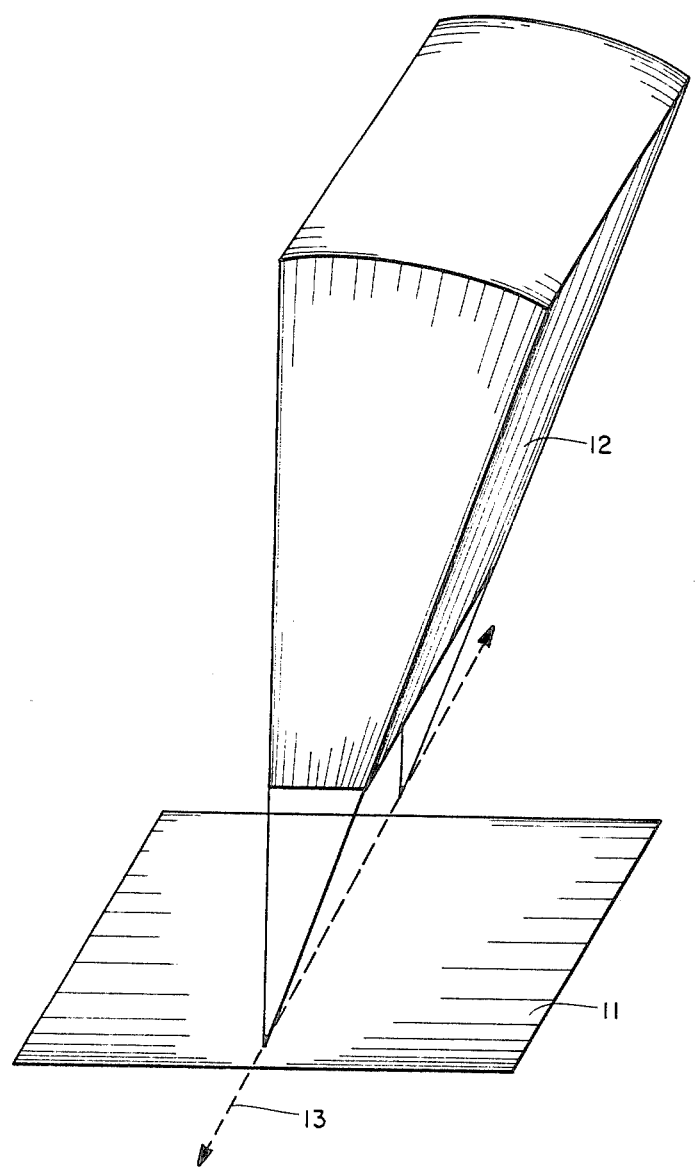
FIG. 1 is a perspective drawing of the support surface and visual surround in a preferred embodiment of the invention.

FIG. 1 shows in perspective a simplified drawing of a preferred embodiment of a device in accordance with the present invention. A movable support surface 11 is rotatable about an axis 13. When a standing subject is placed on the support surface, in accordance with a method of the invention, the axis is made colinear with ankle joints of the subject. Also rotatable about the same axis 13 is the visual surround 12, which provides a surface capable of completely surrounding the field of view of an individual placed on the platform. While standing on the support surface, a subject may also dygrasp a manipulandum which is either fixed to resist voluntary pushes and pulls or can be unexpectedly displaced forward to disturb the subject's equilibrium, as shown in connection with FIGS. 6A-6D below. The support surface and manipulandum may be instrumented with appropriate strain gauges to quantify the reaction forces placed thereon by the subject. Displacement of the body center of mass of the subject with respect to the axis 13 may be measured by means well known in the prior art, such as by coupling the arm of a potentiometer through a linkage to a fastening device worn on the belt of the subject. It will be evident, in the discussion following, that a subject may also assume a position on the support surface so as to straddle the axis 13, i.e., the subject is facing in a direction generally parallel to the axis 13 and thereby subjected to lateral motion about the axis 13.

Figure 1B:
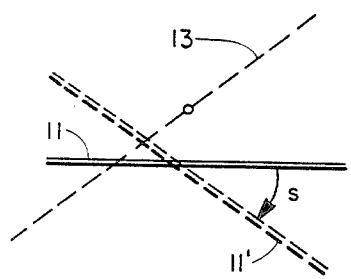
FIG. 1B is a side view detail of the support surface of FIG. 1 and displacement of the support surface about an axis.
Figure 1A:
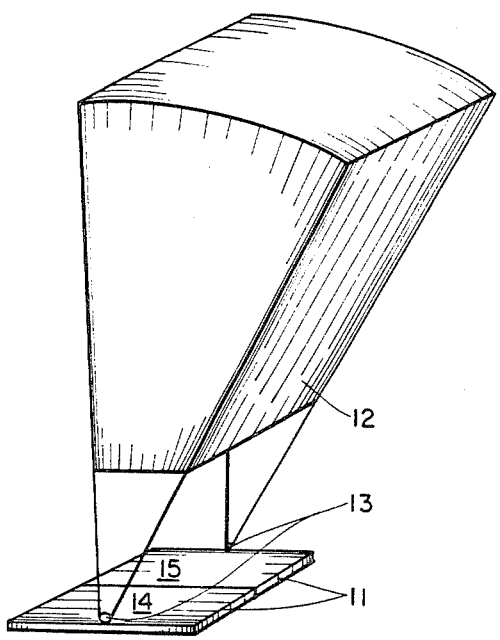
FIG. 1A is a perspective drawing showing another embodiment of the support surface with two independently movable foot supports.

FIG. 1A shows a perspective view of another embodiment of the invention wherein the support surface 11 includes separate components 14 and 15 for supporting each foot of the subject.

In FIG. 1B, there is shown in cross-section the support surface 11 in an initial position and then rotated by an amount S about the axis 13 so as to assume position 11'.

Figure 2:
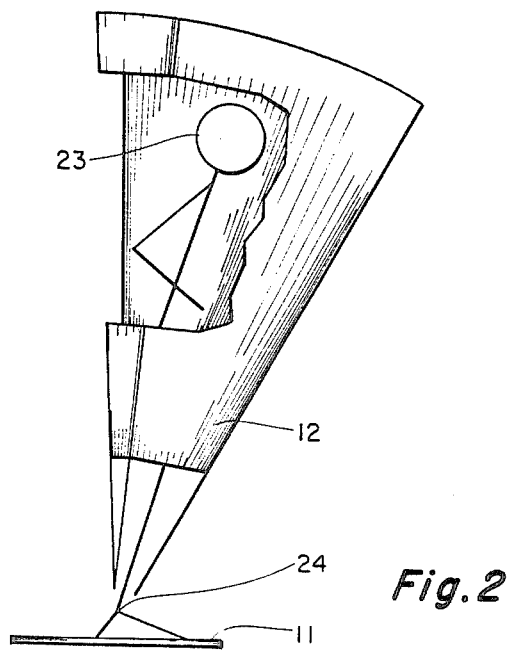
FIG. 2 is a cutaway view showing the placement of a standing subject in relation to the device of FIG. 1 according to one test method.

Referring now to FIG. 2, there is shown a subject 23 standing on a support surface 11 in accordance with the invention. The subject is within the visual surround 12, so that the entire field of view of the subject is surrounded by the visual surround 12. In particular, the individual is standing so as to face the right hand side of the page. The subject's ankle joints 24 are colinear with the axes of rotation of the visual surround 12 and the platform 11. It should be pointed out that (as illustrated in FIGS. 4A, 5A, 6C, and 6D), the subject may also be seated on the platform and still placed within the visual surround. In such instance, it is desirable in many instances to have the axis of rotation of the visual surround and of the support surface to be colinear with the hip joints of the subject. Motion of the support surface and of the visual surround can be caused by means known in the art. In some instances, it may be found suitable to use hydraulic or solenoid actuation under computer control to provide rotation as previously described, whereas in other instances, simpler mechanical systems may also be suitably employed. In any event, the axis of rotation with respect to a subject may be changed by suitably shimming the subject on the support surface or by altering the mechanical operation of the support surface itself.

The invention permits the study of the sensory and motor processes which maintain a subject in the correct orientation with respect to the support surface as the subject attempts to maintain a position of equilibrium on the support surface. The organization of motor responses of a subject may be studied by examining patterns of muscle contractions which stabilize motions of the body of the subject. Referring again to FIG. 2, the subject may stand on the platform in a manner permitting the study of leg muscle contractions which stabilize the antero-posterior (AP) sway motions of the center of body mass. These sway motions frequently occur during free-stance as a consequence of the inherently unstable properties of the upright human body or of the support surface perturbations. During locomotion, unexpected perturbations in orientation arise from similar sources; however, the relation between the center of body mass and the center of foot support is now a dynamic one which is concerned with both the instantaneous ability of the walking subject and his continued forward travel. In contrast, the subject preparing to exert force upon a hand-held manipulandium while standing unsupported has advanced knowledge of the forces which will potentially destabilize the body. In all of the above instances, the forces acting upon the body would lead to instability were it not for the exertion of appropriate compensatory forces by the feet upon the support surface. The invention permits addressing the manner in which compensatory motor actions are initiated following unexpected AP displacements of the body center of mass or in anticipation of voluntary AP disturbances and how these actions are coordinated among a large group of functionally related muscles of the legs, trunk and arms. The invention therefore permits unexpected alterations in the sensory conditions to be used to explore the hierarchical organization of sensory inputs. Specifically, the contributions of individual sensory inputs to equilibrium may be quantified by measuring the equilibrium adjustments of standing subjects deprived of vision and/or support surface inputs.

The invention permits use of waveforms of brief, support-surface movements to disturb the AP equilibrium of the subject. Unexpected, forward or backward displacement of the support surface induces a predictable AP sway rotation principally about the ankle joints and in a direction opposite to that of the platform movement. Sway rotations of the center of body mass about the ankles can be induced in other ways such as unexpectedly rotating the support surface or unexpectedly displacing a hand-held manipulandum, as shown in FIGS. 6A–6D. While each of the above three perturbations involves a very different combination of sensory inputs, each requires a similar compensatory action: contraction of the calf and thigh muscles appropriate to resist forward or backward AP sway displacements of the body center of mass. The above three perturbations have been used to identify an automatic behavior which is common to all AP compensatory actions.

Figure 5:
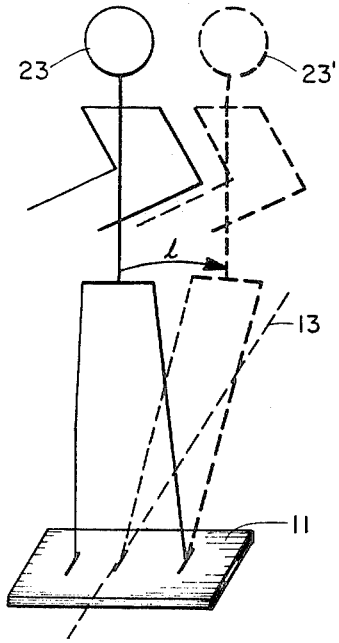
FIG. 5 is a sketch of a subject standing on a support surface in accordance with the invention and facing along the support surface rotation axis.
Figure 5A:
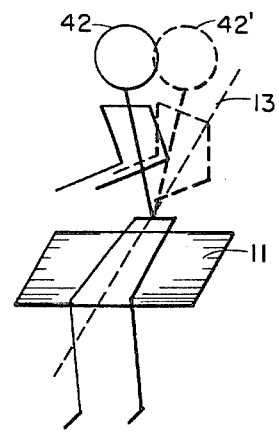
FIG. 5A shows a subject seated on a support surface in accordance with this invention and facing along the support surface rotation axis.

Unexpected rotation of the support surface about an axis 13 such as illustrated in FIG. 5 straddled by the subject produces a very different motion. The body sways laterally to the side of the lowering leg. This condition requires a very different compensatory action from that described above for AP sway perturbations; the lowering leg is actively extended and the elevating leg actively flexed to maintain the appropriate distribution of lateral forces.

Figure 3:
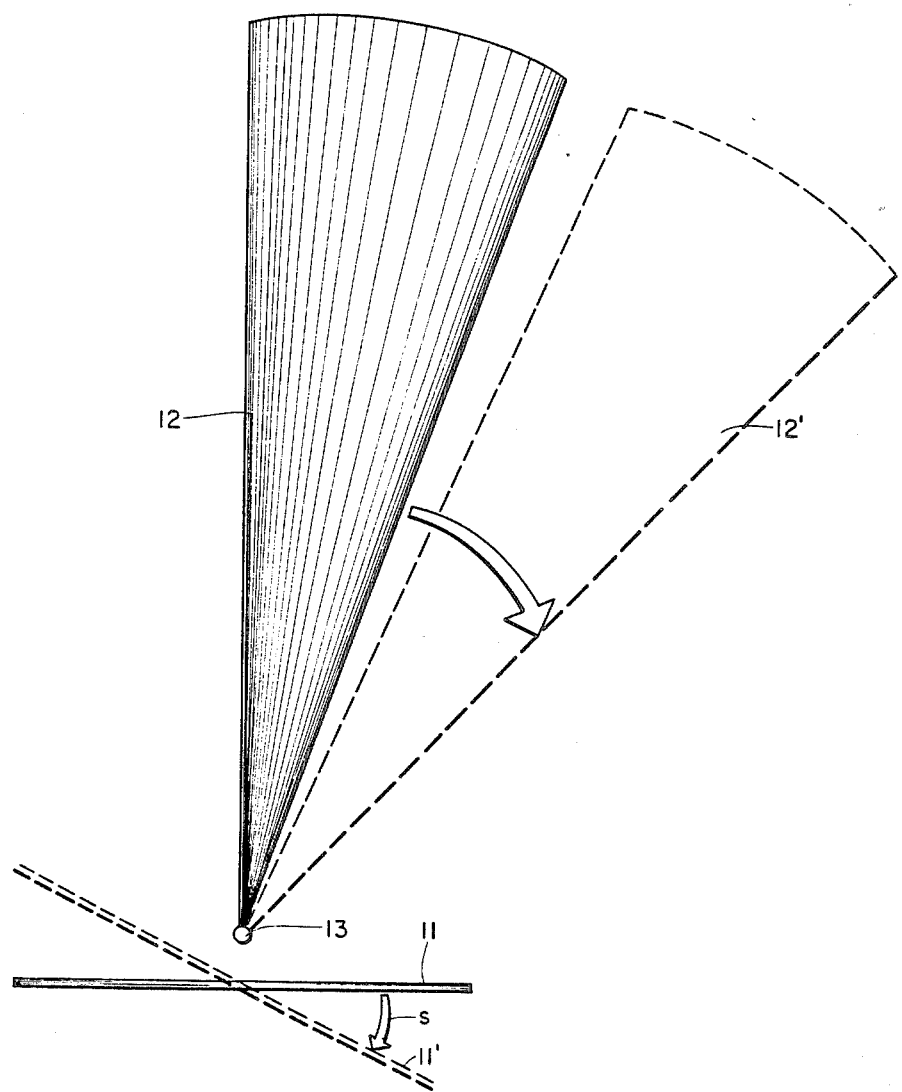
FIG. 3 is a drawing of the support surface and visual surround of FIG. 1 in displaced and undisplaced positions.
Figure 4:
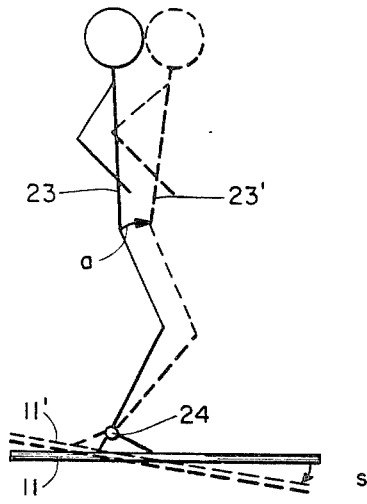
FIG. 4 is a sketch of a subject standing on a support surface in accordance with the invention indicating the alignment of the subject's ankle joints with the support surface rotation axis and showing the measured anteroposterior sway angle.
Figure 4A:
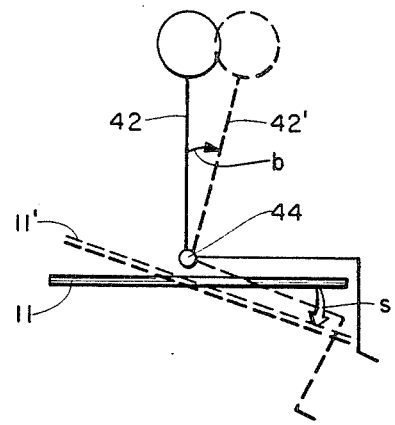
FIG. 4A shows a subject in the seated position upon the support surface, indicating the alignment of the subject's hip joints with the support surface rotation axis and the corresponding measured anteroposterior sway angle.

While the information from support surface and visual inputs may be perceptually correct at all times, the sense of orientation derived from the support surface and visual inputs can be altered by moving the surfaces continuously. While the position of the ankle joints with respect to the support surface provides useful vertical information under fixed surface conditions, this input can be reduced to below threshold levels by a procedure I call "support surface stabilization". Under this unusual condition, the platform support surface is caused to rotate in direct proportion to changes in the measured AP orientation of the center of body mass, so that the relative orientation of the subject and support surface is fixed. I have found that a similar procedure may be used to approximately eliminate the normal swayrelated movements of the subject with respect to his visual surround, and term this technique "visual stabilization". (Although discussion of support surface stabilization and visual stabilization has been principally with respect to AP sway, it will be seen that stabilization may also occur with respect to lateral sway in an analagous manner.) In FIG. 3 the manner of stabilization is indicated, wherein a displacement of the support surface 11 about axis 13 by an amount s is matched by a corresponding displacement v of the visual surround. I have found that when there is both visual stabilization and support surface stabilization, the subject must rely substantially on the vestibular system in order to maintain equilibrium.

I have developed a protocol for categorizing a a subject's independent ability to maintain a position in equilibrium by appropriate organization of sensory orientation inputs. As an example, let us consider orientation of a standing subject with respect to AP sway motion. Two important criteria may be identified in the process of categorization. The first criterion I term "direct sensory control", which is the ability of an individual to stand while AP support surface inputs and visual inputs are simultaneously disrupted. The second criterion I term "adaptive sensory control", which is the ability of a subject to stand while AP support surface inputs are disrupted and the subject is simultaneously exposed to incorrect visual inputs. In accordance with these criteria, I have identified four significant categories for a subject's ability to organize sensory orientation inputs. These categories are identified in Table I. Category I is reserved for subjects who are abnormal according to both direct sensory control and adaptive sensory control criteria. Category II is reserved for subjects whose direct sensory control is within normal limits but whose adaptive sensory control is outside normal limits. Category III is reserved for subjects who have mild abnormalities in either direct or adaptive sensory control criteria, and Category N is reserved for all other subjects.

Utilizing my invention, relatively straightforward test procedures can measure direct sensory control and adaptive sensory control. Assuming that a subject is able to maintain balance on the support surface, one can obtain in each case what I call an "index of stability". Generally, an individual who loses balance under the test for direct sensory control will be unable to maintain balance in the test for adaptive sensory control. Because of these factors, and in order to obtain more information concerning a subject, it is sometimes desirable to precede the test for these two criteria with a simpler test of a subject's ability to maintain equilibrium with eyes open on a stabilized support surface. Let us define this last test as Procedure X defined as follows:

A. Stand the subject on a support surface such as shown in FIG. 2, which is rotatable about an axis colinear with the subject's ankle joints.

B. Measure the change in the subject's AP sway angle.

C. Cause the support surface to undergo a change in angular orientation about the rotation axis so as to equal the measured change in the subject's orientation angle, thereby nullifying changes in the angle between the orientation of the subject and the inclination of the support surface. (In this Procedure, the visual surround 12 of FIG. 2 is kept stationary with respect to the earth.)

D. Determine whether the subject independently maintains a position in equilibrium on the support surface.

E. If the subject maintains a position in equilibrium over a specified time interval, compute a quantity related to the average amplitude of changes in the measured AP stance orientation angle during the specified interval of time. This quantity is termed the "index of stability".

Although the index of stability is related to the average amplitude of changes in the AP stance orientation angle, I have found it convenient to take the AP sway record, subject it to full-wave rectification, and numerically integrate the result after removal of the DC (steady state) bias. When these results are normalized, comparisons may be made in a straightforward manner. Such results are embraced within the meaning of "index of stability" as used in this Description and in the following claims.

Test Procedure Y permits measurement of direct sensory control. Under Test Procedure Y, the subject experiences support surface stabilization while being deprived of visual input. This is accomplished by following Test Procedure X with the modification that the subject stands with eyes closed or blindfolded.

Test Procedure Z addresses adaptive sensory control, and under this procedure the subject experiences both support surface stabilization and visual stabilization.

In this procedure, the subject stands on a support surface as shown in FIG. 2, and the support surface is stabilized in the manner discussed in connection with Procedure X. Furthermore, the visual surround is also stabilized, i.e., caused to undergo a change in angular orientaton about the rotation axis so that any change in its angle matches the measured change in the subject's AP sway, thereby nullifying changes in angle between the orientation of the subject and the orientation of the visual surround.

In procedures Y and Z an index of stability may also be computed as a quantity related to the average amplitude of changes in the measured AP stance orientation angle during the specified interval of time for each procedure. The index of stability of Procedure Y ($I_Y$) I sometimes call, in this description and the following claims, the "index of blind stability." The index of stability for Procedure Z ($I_Z$) I sometimes call, in this description and the claims, the "index of visually disinformed stability."

Table II summarizes how a subject's ability in organizing sensory orientation inputs may be categorized according to Test Procedures Y and Z. A subject is placed in category I who loses balance in procedures Y and Z.

TABLE I

| Category | Direct Sensory Control | Adaptive Sensory Control |
| --- | --- | --- |
| I | Abnormal | Abnormal |
| II | Normal | Abnormal |
| III | Normal or Mildly Abnormal | Mildly Abnormal or Normal |
| N | Normal | Normal |

TABLE II

| Category | Procedure Y | Procedure Z |
| --- | --- | --- |
| I | loses balance | loses balance |
| II | upright | loses balance or $I_Z \geq 1.5\, I_Y$ |
| III | upright high $I_Y$ | upright high $I_Z$ |
| N | Normal | Normal |

A subject who maintains an upright position in procedure Y but loses balance in procedure Z, or who maintains an upright standing position of equilibrium in procedures Y and Z but has an index of visually disinformed stability at least 1.5 times as great as the index of blind stability, is placed in category II. A subject is placed in category III who maintains a position of equilibrium in procedures Y and Z if the indices of blind stability and visually disinformed stability fall above the range of values for an age-matched normal population of subjects according to a statistical criterion of significance. All other subjects are placed in category N.

It will be apparent that the procedures X, Y, and Z in connection with measurement of stability in the AP plane may be modified for use in other planes or with the subject in positions in equilibrium other than standing. In each case, it is of significance that these procedures deal first with support surface stabilization alone (although this step may be omitted), then with support surface stabilization and a subject deprived of visual input as by being blindfolded, and then with both support surface stabilization and visual stabilization. The procedures may be applicable to subjects in positions of seated equilibrium, for example, in either the AP or lateral planes.

Moreover, the stabilization of the support surface and/or of the visual surround need not be accomplished simply by causing the change of orientation of these stabilized surfaces to match exactly the sway of the subject. The stabilized surface may be caused to change orientation, for example, by 0.5 times the sway of the subject. Setting this stabilization gain to 0.5 in a test may permit some subjects to maintain balance who would otherwise lose balance in a test utilizing a stabilization gain of 1.0. Accordingly a series of tests may employ successively higher stabilization gains.

Figure 7:
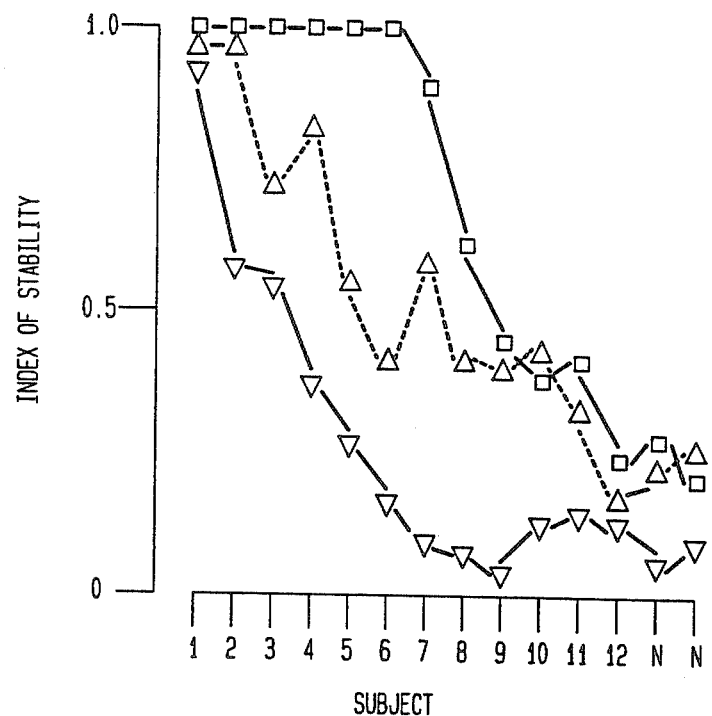
FIG. 7 is a graph showing indices of stability for a number of pathological and normal subjects experiencing Test Procedures X, Y, and Z as discussed below.

FIG. 7 shows indices of stability for a group of subjects experiencing Test Procedures X, Y, and Z with respect to AP sway. With eyes open (Procedure X) all except subject 1 maintained balance with a stabilizing gain of 1.0, the level at which relative sway motions between the subject and the support surface were eliminated completely. Subject 1 maintained stability only when gains were 0.8 or less. Eye-closure (Procedure Y) increased the index of stability of all participants. (An index of 1.0 indicates inability to maintain balance, whereas a lower index indicates relatively greater ability of the subject to maintain equilibrium.) Nevertheless, all but subjects 1 and 2 continued to maintain balance with stabilizing gains of 1.0. With eyes closed, the maximum stabilizing gain achieved by subject 1 decreased to 0.70, while that of subject 2 was 0.8. When subsequently reopening their eyes under stabilized visual conditions (Test Procedure Z), subjects 3 to 6 (who had just completed this task successfully with their eyes closed) now lost balance, while the index of stability of subjects 7 and 8 increased to near the stable limits. Under Test Procedure Z, the maximum gains at which patients 1 to 6 could remain stable all ranged between 0.7 and 0.8.

Figure 8:
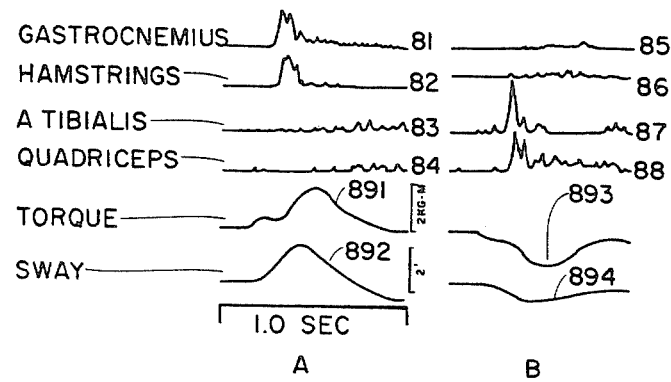
FIG. 8 depicts the electromyographic signal traces from the four indicated leg muscles of a subject standing upon a support surface according to the invention and subjected to a forward anteroposterior sway perturbation (side A) or backward anteroposterior sway perturbation (side B) without "stabilization" of the support surface or the visual surround.

Further details of the clinical information obtainable in accordance with methods and devices of the present invention may be seen in FIG. 8. This figure shows typical electromyographic signal traces 81-88 from four leg muscles of a typical standing subject as the subject regains equilibrium following an anteroposterior rotational displacement of the support surface. There are also plotted the restoring torque 891,893 and the angular amplitude of sway 892,894 of the subject over the corresponding one-second time interval following perturbation. This data permits a simple tabulation of the specific muscles involved in correcting forward (side A) and backward sway (side B), the relative strength of such muscle responses, and the timing thereof. By techniques of graphic analysis, or direct computation from the underlying signal traces, this quantifying data may be quickly analyzed or displayed for comparison with corresponding data of other subject populations. It can also be seen from the torque and AP sway records of this figure that the subject's musculature generated resistive forces sufficient to arrest AP sway (full scale 2°) within 1 second.

The ready compilation of this data further allows a more complete understanding of a given subject's visually observed postural responses. For instance one may quickly distinguish the equilibrium which results from a subject's small but timely responses of appropriate muscles to small sway perturbations, as shown in FIG. 8, from an inappropriate contracting of all postural muscles of a subject lacking normal coordination. Under small perturbations, the general mechanical stiffening of the latter would result in a degree of stability which might appear clinically normal on simple visual inspection. The dynamic correlation of support motions, muscle signal traces and normal responses permits a quick differentiation of such conditions, and would promptly single out the abnormal subject in a clinical setting for appropriate further testing.

Figure 9:
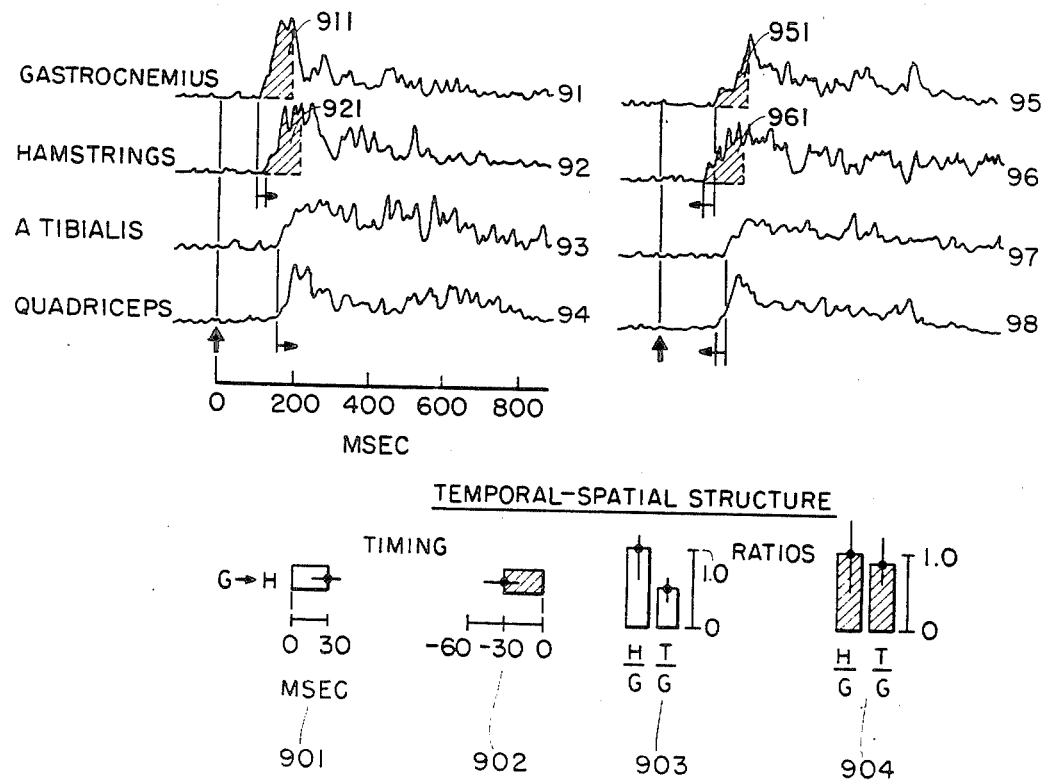
FIG. 9 depicts the electromyographic signal traces from four leg muscles in each leg of a spastic hemiplegic subject standing upon a support surface and caused to undergo anteroposterior sway by a backward support surface dispacement according to the invention.

Use of the invention for computing temporal and spatial parameters of muscle coordination is illustrated in FIG. 9 in which ensemble averaged EMG, torque, and AP sway records of the less-involved and the spastic legs in a spastic hemiplegic subject are compared in response to forward sway perturbations. Forward sway rotations of the body about the ankle joints were compensated in the less-involved leg by contraction of the stretching gastrocnemius muscle (record 91), latency 97±5 msec (mean ±S.D.). Mechanically coupled motions of the hips were stabilized by contraction of the synergist hamstrings muscle (record 92) beginning on the average 26±12 msec (mean ±S.D.) later than in the gastrocnemius. The sequence of muscle activation beginning distally at the base of support and radiating proximally away from the support is highlighted in the figure by the rightward pointing arrow relating the relative latencies of gastrocnemius and hamstrings muscles, while the relative strengths of gastrocnemius and hamstrings contractions during the first 75 msec of response (numerical integral of EMG signals) are illustrated by the shaded areas 911 and 921 respectively. This temporal and spatial structuring of EMG response to forward sway perturbations is the same as that observed in normal adults and normal juveniles aged 1½ to 10 years.

The pattern of contraction within muscles of the spastic leg shown in FIG. 9 was significantly different than that described above. Latency of gastrocnemius response (record 95) was slower (145±13 msec), and the sequence of activity was temporally reversed beginning in the hamstrings (record 96) and then radiating distally towards the base of support as indicated by the negative sequence value (−31±25 msec) and the leftward pointing arrow relating relative latencies of gastrocnemius and hamstrings muscles. Note that subsequent activation of the anterior tibialis (records 93 and 97) and quadriceps muscles (record 94 and 98), antagonists which helped brake the return sway movement, were sequenced in the non-involved leg beginning at base of support and then radiating upward, while the reverse sequence of antagonist activation was again observed in muscles of the spastic leg.

Methods of the present invention for quantifying, separately in the less-involved and in the spastic leg, three parameters of muscular coordination are introduced under the "Structure" heading below the EMG traces. In the parameterization of the temporal structuring of response, positive "timing" values (shown in item 901) of the less-involved leg indicate that activity commenced in the ankle joint muscles (closest to base of support) and then radiated proximally to the upper leg synergists. In contrast, the negative values of spastic leg (shown in item 902) contractions depict the opposite proximal to distal sequence of activation. In the parameterization of the spatial structuring of response, the standard deviation of the mean H/G ratio quantifies the degree of fixation in the relative activation strengths of distalproximal synergists during the initial 75 msec of response. Another spatial parameter, the T/G ratio, characterizes the level of co-activation of the antagonist ankle muscle during this interval of the response. Compared to the less-involved leg (open bars in item 903), the linkages between synergists in the spastic leg (shaded bars in item 904) were 3½ times more variable (larger S.D. of H/G ratio), and the level of coactivation of the antagonist was over twice as great (larger T/G ratio).

Similar results were obtained for this subject when subject to backward sway perturbations (support surface displaced forward). When parameters quantifying the temporal and spatial structure of automatic postural adjustments to such perturbations were distilled from the EMG records of the subject, the distribution of normal and abnormal parameters was identical to that shown in FIG. 9. Compared to the less involved leg, the temporal order of activation in the spastic leg was reversed, the linkage between synergists was much more variable, and the level of antagonist co-activation was greater.

The imposition of support surface rotations and the voluntary exertion of force against a hand-held manipulandum in accordance with, for example, FIG. 6A, are two additional paradigms that may be used to assess parameters of muscle coordination in accordance with procedures analogous to those discussed above in connection with FIG. 9. Referring to FIG. 6A, the subject may be instructed to voluntarily pull or push upon the handle 55 upon the commencement of a tone. Such tone-triggered voluntary pulls and pushes are movements which displace the body center of mass forward and backward respectively, but in a manner accompanied by a very different configuration of sensory inputs in comparison to simple translation of the support surface. Depsite gross differences in the way postural adjustments were elicited in instances such as described in this paragraph, the coordination parameters obtained correspond closely to those obtained from tests described in connection with FIG. 9. In contrast to the less-involved side of the body, activation sequences of spastic leg and arm muscles were in all instances temporally reversed. On the spastic side during platform surface rotations, the proximal muscles were activated in advance of their distal synergists, even though the stimuli in these instances consisted of isolated stretch of the distal ankle joint muscle. Similarily, leg muscles on the spastic side did not respond in anticipation of postural disturbances caused by voluntary pulls and pushes.

Accordingly, the sequencing of muscle activity and spatial ratio parameters of coordination illustrated in connection with FIG. 9 are useful in isolating abnormal patterns of muscle activity.

It will be appreciated that the invention may be used in a variety of applications in fashion analogous to that described above. For example, the manipulandum 55 shown in FIGS. 6A and 6C is being moved in the AP sway plane. It may also be moved horizontally, as shown in FIGS. 6B and 6D in a plane orthogonal to the AP sway plane, i.e., laterally. Furthermore, although FIGS. 8 and 9 relate to use of leg muscles, muscles in the arm and other portions of the body may also be considered as postural muscles in appropriately created tests in a fashion analogous with the methods described above.

Accordingly, while the invention has been described with reference to specific embodiments, it will be appreciated that it may be embodied in a variety of forms diverse from those shown without departing from the spirit and scope of the following claims.

What is claimed is:

1. A method for testing whether a subject's ability to maintain position in equilibrium in a selected plane of motion is grossly abnormal with respect to both of two criteria, where the first criterion (termed "direct sensory control criterion") is the ability to maintain equilibrium position while support surface inputs and visual inputs related to motion in the selected plane are simultaneously disrupted, and the second criterion (termed "adaptive sensory control criterion") is the ability to maintain equilibrium position while surface inputs related to motion in the selected plane are disrupted and the subject is simultaneously exposed to incorrect visual inputs, and such method comprising:

(1) Performing Test Procedure Y as follows:
  (A) placing the subject in a position of equilibrium on a support surface which is independently rotatable about an axis (hereinafter the "support surface rotation axis") related to the subject's position in equilibrium and having the subject stand with eyes closed or blindfolded;
  (B) measuring change (hereinafter termed "change in the subject's orientation angle") in the angular orientation of the subject in the selected plane of motion;
  (C) causing the support surface to undergo a change in angular orientation about the support surface rotation axis so as to equal the measured change in the subject's orientation angle, thereby nullifying changes in angle between the orientation of the subject and the inclination of the support surface;
  (D) determining whether or not the subject independently maintains the position in equilibrium;
(2) Performing Test Procedure Z as follows:
(A) placing the subject in a position in equilibrium on a support surface which is independently rotatable about an axis (hereinafter the "support surface rotation axis");
  (B) substantially surrounding the subject's field of view of a movable second surface (hereinafter the "visual surround");
  (C) measuring the change in the subject's orientation angle;
  (D) causing the support surface to undergo a change in angular orientation about the support surface rotation axis so as to equal the measured change in subject's orientation angle, thereby nullifying changes in angle between the orientation of the subject and the inclination of the support surface;
  (E) causing the visual surround to undergo a change in angular orientation about the support surface rotation axis so as to equal the measured change in subject's orientation angle, thereby nullifying changes in angle between the orientation of the subject and the orientation of the visual surround; and
  (F) determining whether or not the subject independently maintains the position in equilibrium.

2. A method according to claim 1, for testing whether a subject's ability to maintain an upright standing position in equilibrium by appropriately organizing sensory orientation inputs in the anteroposterior plane of motion is grossly abnormal with respect to both direct sensory criteria and adaptive criteria, wherein Step A of Test Procedure Y and Step A of Test Procedure Z each include the further step of standing the subject on a support surface with the support surface rotation axis colinear with the axis defined by subject's ankle joints, and wherein Step B of Test Procedure Y and Step C of Test Procedure Z each include the further step of measuring the change in the angular orientation of the subject's center of body mass in the anteroposterior plane around the axis defined by the subject's ankle joints, and wherein the method further comprises:
  (3) identifying as grossly abnormal with respect to direct sensory control and with respect to adaptive sensory control each subject who fails to maintain equilibrium in step D of Test Procedure Y and also fails to maintain equilibrium in step F of Test Procedure Z.

3. A method according to claim 1, for testing whether a subject's ability to maintain an upright seated position in equilibrium by appropriately organizing sensory orientation inputs in the anteroposterior plane of motion is grossly abnormal with respect both direct sensory criteria and adaptive criteria, wherein step A of Test Procedure Y and step A of Test Procedure Z each include the step of seating the subject on a support surface with the support surface rotation axis colinear with the axis defined by the subject's hip joints, and wherein step B of Test Procedure Y and step C of Test Procedure Z each includes the further step of measuring the change in the angular orientation of the subject's trunk in the anteroposterior plane around the axis defined by the subject's hip joints, and wherein the method further comprises:
  (3) Identifying as grossly abnormal with respect to direct sensory control and with respect to adaptive sensory control each subject who fails to maintain equilibrium in step D of test procedure Y and also fails to maintain equilibrium in step F of test procedure Z.

4. A method according to claim 1, for testing whether a subject's ability to maintain an upright standing position in equilibrium by appropriately organizing sensory orientation inputs in the lateral plane of motion is grossly abnormal with respect both direct sensory criteria and adaptive criteria, wherein step A of Test Procedure Y and step A of Test Procedure Z each include the further step of standing the subject on a support surface, with the support surface rotation axis perpendicular to the line segment defined by the subject's ankle joints at the center point of said segment, wherein step B of Test Procedure Y and step C of Test Procedure Z each include the further step of measuring the change in the angular orientation of the subject's center of body mass in the lateral plane around the support surface rotation axis, and wherein the method further comprises:
  (3) identifying as grossly abnormal with respect to direct sensory control and with respect to adaptive sensory control each subject who fails to maintain equilibrium in step D of Test Procedure Y and also fails to maintain equilibrium in step F of Test Procedure Z.

5. A method according to claim 1, for testing whether a subject's ability to maintain an upright seated position in equilibrium by appropriately organizing sensory orientation inputs in the lateral plane of motion is grossly abnormal with respect to both direct sensory criteria and adaptive criteria, wherein step A of Test Procedure Y and step A of Test Procedure Z each include the further step of seating the subject on a support surface with the support surface rotation axis perpendicular to the line segment defined by the subject's hip joints at the center point of such sement, and wherein step B of Test Procedure Y and step C of Test Procedure Z each include the further step of measuring the change in the angular orientation of the subject's trunk in the lateral plane around the support surface rotation axis, and wherein the method further comprises:

(3) Identifying as grossly abnormal with respect to direct sensory control and with respect to adaptive sensory control each subject who fails to maintain equilibrium in step D of test procedure Y and also fails to maintain equilibrium in step F of test procedure Z.

6. A method for testing whether a subject's ability to maintain a position in equilibrium by appropriately organizing sensory orientation inputs in a selected plane of motion according to two criteria is normal with respect to the first criterion but grossly abnormal with respect to the second criterion, where the first criterion (termed "direct sensory control criterion") is the ability to maintain equilibrium position while support surface input and visual inputs are simultaneously disrupted, and the second criterion (termed "adaptive sensory control criterion") is the ability to maintain equilibrium position while surface inputs are disrupted and the subject is simultaneously exposed to incorrect visual inputs, such method comprising:

(1) Performing Test procedure X as follows:
(A) placing the subject in a position in equilibrium on a support surface which is independently rotatable about an axis (hereinafter the "support surface rotation axis") related to the subject's position in equilibrium;
(B) measuring the change (hereinafter termed "change in subject's orientation angle") in the angular orientation of the subject in the selected plane of motion;
(C) causing the support surface to undergo a change in angular orientation about the support surface rotation axis so as to equal the measured change in the subject's orientation angle, thereby nullifying changes in angle between the orientation of the subject and the inclination of the support surface;
(D) determining whether or not the subject independently maintains the position in equilibrium.

(2) Performing Test Procedure Y as follows:
(A) placing the subject in a position in equilibrium on a support surface which is independently rotatable about an axis (hereinafter the "support surface rotation axis") related to the subject's position in equilibrium, and having the subject stand with eyes closed or blindfolded;
(B) measuring the change in the subject's orientation angle;
(C) causing the support surface to undergo a change in angular orientation about the support surface rotation axis so as to equal the measured change in the subject's orientation angle, thereby nullifying changes in angle between the orientation of the subject and the inclination of the support surface;
(D) determining whether or not the subject independently maintains the position in equilibrium.
(E) determining, if the subject maintains the position in equilibrium over a specified time interval, an index of stability for this Test Procedure Y, such index termed the "index of blind stability," related to the average amplitude of change in the measured subject's orientation angle during the specified interval of time;

(3) Performing Test Procedure Z as follows:
(A) placing the subject in a position in equilibrium on a support surface which is independently rotatable about an axis (hereinafter the "support surface rotation axis") related to subject's position in equilibrium;
(B) substantially surrounding the subject's field of view with a second surface (hereinafter the "visual surround") independently movable with respect to the support surface;
(C) measuring the change in the subject's orientation angle;
(D) causing the support surface to undergo a change in angular orientation about the support surface rotation axis so as to equal the measured change in the subject's orientation angle, thereby nullifying changes in angle between the orientation of the subject and the inclination of the support surface;
(E) causing the visual surround to undergo a change in angular orientation about the support surface rotation axis so as to equal the measured change in the subject's orientation angle, thereby nullifying changes in the angle between the orientation of the subject and the AP orientation of the visual surround;
(F) determining whether or not the subject independently maintains the position in equilibrium;
(G) determining, if the subject maintains the position in equilibrium over a specified time interval, an index of stability for this Test Procedure Z, such index termed the "index of visually disinformed stability," related to the average amplitude of change in the measured subject's orientation angle during the specified interval of time.

7. A method according to claim 6, for testing whether a subject's ability to maintain an upright standing position in equilibrium by appropriately organizing sensory orientation inputs in the anteroposterior plane of motion is normal with respect to direct sensory control criteria but grossly abnormal with respect to adaptive sensory control criteria, wherein step A of each of Test Procedures X, Y, and Z includes the further step of standing the subject on a support surface with the support surface rotation axis colinear with the axis defined by subject's ankle joints, and wherein step B of Test Procedure X, step B of Test Procedure Y and step C of Test Procedure Z each includes the further step of measuring the change in the angular orientation of the subject's center of body mass in the anteroposterior plane around the axis defined by the subject's ankle joints, and wherein the method comprises:

(4) identifying as normal with respect to direct sensory control but grossly abnormal with respect to adaptive sensory control each subject who has maintained a position in equilibrium in Test X and Test Y but not in Test Z; and (5) identifying as normal with respect to direct sensory control but grossly abnormal with respect to adaptive sensory control each subject who has maintained a position in equilibrium in Test X, Test Y, and Test Z but whose index of visually disinformed stability is at least approximately 1.5 times as great as his index of blind stability.

8. A method according to claim 6, for testing whether a subject's ability to maintain an upright standing position in equilibrium by appropriately organizing sensory orientation inputs in the anteroposterior plane of motion is mildly abnormal with respect to either direct sensory control criteria or adaptive sensory control criteria, wherein Step A of each of Test Procedures X, Y, and Z includes the further step of standing the subject on a support surface with the support surface rotation axis colinear with the axis defined by subject's ankle joints, and wherein step B of Test Procedure X, step B of Test Procedure Y and step C of Test Procedure Z each includes the further step of measuring the change in the angular orientation of the subject's center of body mass in the anteroposterior plane around the axis defined by the subject's ankle joints, and wherein the method further comprises:

(4) identifying as mildly abnormal with respect to direct sensory control or with respect to adaptive sensory control each subject who maintains a position in equilibrium in step D of Test Procedure X, step D of Test Procedure Y and also step F of Test Procedure Z whose index of blind stability and whose index of visually disinformed stability are each above the range of values for an age-matched normal population of subjects according to a statistical criterion of significance.

9. A method according to claim 6, for testing whether a subject's ability to maintain an upright standing position in equilibrium by appropriately organizing sensory orientation inputs in the anteroposterior plane of motion is grossly normal, wherein step A of each of Test Procedures X, Y, and Z includes the further step of standing the subject on a support surface with the support surface rotation axis colinear with the axis defined by the subject's ankle joints, and wherein step B of Test Procedure Y and step C of Test Procedure Z each include the further step of measuring the change in the angular orientation of the subject's center of body mass in the anteroposterior plane around the axis defined by the subject's ankle joints, and wherein the method further comprises:

(4) determining if the subject has maintained equilibrium in step D of Test Procedures X and Y and in step F of Test Procedure Z and also has an index of visually disinformed stability at least approximately 1.5 times as great as his index of blind stability;

(5) determining if the subject has maintained equilibrium in step D of each of Test Procedures X and Y and in step F of Test Procedure Z and also has an index of visually disinformed stability and an index of blind stability whose values are each above the range of values for an age-matched normal population of subjects according to a statistical criterion of significance;

(6) identifying as grossly normal each subject who satisfies the conditions of steps (4) and (5).

10. A method according to claim 6, for testing whether a subject's ability to maintain an upright seated position in equilibrium by appropriately organizing sensory orientation inputs in the anteroposterior plane of motion is normal with respect to direct sensory control criteria but grossly abnormal with respect to adaptive sensory control criteria, wherein step A of each of Test Procedures X, Y, and Z includes the further step of seating the subject on a support surface with the support surface axis colinear with the axis defined by the subject's hip joints, and wherein each of step B of Test Procedure X, step B of Test Procedure Y and step C of Test Procedure Z includes the further step of measuring the change in the angular orientation of the subject's trunk in the anteroposterior plane around the axis defined by the subject's hip joints and wherein the method further comprises:

(4) identifying as normal with respect to direct sensory control but grossly abnormal with respect to adaptive sensory control each subject who has maintained a position in equilibrium in Test X and Test Y but not in Test Z;

(5) identifying as normal with respect to direct sensory control but grossly abnormal with respect to adaptive sensory control each subject who has maintained a position in equilibrium in Test X, Test Y and Test Z but whose index of visually disinformed stability is at least approximately 1.5 times as great as his index of blind stability.

11. A method according to claim 6, for testing whether a subject's ability to maintain an upright seated position in equilibrium by appropriately organizing sensory orientation inputs in the anteroposterior plane of motion is mildly abnormal with respect to either direct sensory control criteria or adaptive sensory control criteria, wherein step A of each of Test Procedures X, Y, and Z includes the further step of seating the subject on a support surface with the support surface axis colinear with the axis defined by the subject's hip joints, and wherein each of step B of Test Procedure X, step B of Test Procedure Y and step C of Test Procedure Z includes the further step of measuring the change in the angular orientation of the subject's trunk in the anteroposterior plane around the axis defined by the subject's hip joints, and wherein the method further comprises:

(4) identifying as mildly abnormal with respect to direct sensory control or with respect to adaptive sensory control each subject who maintains a position in equilibrium in step D of Test Procedure X, step D of Test Procedure Y and also step F of Test Procedure Z whose index of blind stability and whose index of visually disinformed stability are each above the range of values for an age-matched normal population of subjects according to a statistical criterion of significance.

12. A method according to claim 6, for testing whether a subject's ability to maintain an upright seated position in equilibrium by appropriately organizing sensory orientation inputs in the anteroposterior plane of motion is grossly normal, wherein step A of each of Test Procedures X, Y and Z includes the further step of seating the subject on a support surface with the support surface rotation axis colinear with the axis defined by the subject's hip joints, and wherein step B of Test Procedure Y and step C of Test Procedure Z each include the further step of measuring the change in the angular orientation of the subject's trunk in the anteroposterior plane around the axis defined by the subject's hip joints, and wherein the method further comprises:

(4) determining if the subject has maintained equilibrium in step D of each of Test Procedures X and Y and in step F of Test Procedure Z and also has a index of usually disinformed stability at least 1.5 times as great as his index of blind stability;

(5) determining if the subject has maintained equilibrium in step D of each of Test Procedures X and Y and in step F of Test Procedure Z and also has an index of visually disinformed stability and an index of blind stability whose values are above the range of values of an age-matched normal population of subjects according to a statistical criterion of significance.

(6) identifying as grossly normal each subject who satisfies the conditions of steps (4) and (5).

13. A method according to claim 6, for testing whether a subject's ability to maintain an upright standing position in equilibrium by appropriately organizing sensory orientation inputs in the lateral plane of motion is normal with respect to direct sensory control criteria but grossly abnormal with respect to adaptive sensory control criteria, wherein step A of Test Procedures X, Y, and Z each includes the further step of standing the subject on a support surface with the support surface axis perpendicular to the line segment defined by the subject's ankle joints, at the center point of said segment, and wherein step B of Test Procedure X, step B of Test Procedure Y and step C of Test Procedure Z each include the further step of measuring the change in the angular orientation of the subject's center of body mass in the lateral plane around the support surface rotation axis, and wherein the method further comprises:

(4) identifying as normal with respect to direct sensory control but grossly abnormal with respect to adaptive sensory control each subject who has maintained a position in equilibrium in Test X and Test Y but not in Test Z;

(5) identifying as normal with respect to direct sensory control but grossly abnormal with respect to adaptive sensory control each subject who has maintained a position in equilibrium in Test X, Test Y and Test Z but whose index of visually disinformed stability is at least approximately 1.5 times as great as his index of blind stability.

14. A method according to claim 6, for testing whether a subject's ability to maintain an upright standing position in equilibrium by appropriately organizing sensory orientation inputs in the lateral plane of motion is midly abnormal with respect to either direct sensory control criteria or adaptive sensory control criteria, wherein step A of each of Test Procedures X, Y, and Z includes the further step of standing the subject on a support surface with the support surface axis perpendicular to the line segment defined by the subject's ankle joints, at the center point of said segment, and wherein step B of Test Procedure X, step B of Test Procedure Y and step C of Test Procedure Z each include the further step of measuring the change in the angular orientation of the subject's center of body mass in the lateral plane around the support surface rotation axis, and wherein the method further comprises:

(4) identifying as mildly abnormal with respect to direct sensory control or with respect to adaptive sensory control each subject who maintains a position in equilibrium in step D of Test Procedure X, step D of Test Procedure Y and also Step F of Test Procedure Z whose index of blind stability and whose index of visually disinformed stability are each above the range of values for an age-matched normal population of subjects according to a statistical criterion of significance.

15. A method according to claim 6, for testing whether a subject's ability maintain an upright standing position in equilibrium by appropriately organizing sensory orientation inputs in the lateral plane of motion is grossly normal, wherein step A of each of Test Procedures X, Y and Z includes the further step of standing the subject on a support surface with the support surface rotation axis perpendicular to the line segment defined by the subject's ankle joints at the center point of said segment, and wherein step B of Test Procedures X and Y and step C of Test Procedure Z each include the further step of measuring the change in the angular orientation of the subject's center of body mass in the lateral plane around the support surface rotation axis, and wherein the method further comprises:

(4) determining if the subject has maintained equilibrium in step D of each of Test Procedures X and Y and in step F of Test Procedure Z and also has a index of visually disinformed stability of at least approximately 1.5 times as great as his index of blind stability;

(5) determining if the subject has maintained equilibrium in step D of each of Test Procedures X and Y and in step F of Test Procedure Z and also has an index of visually disinformed stability and an index of blind stability whose values are above the range of values for an age-matched normal population of subjects according to a statistical criterion of significance;

(6) identifying as grossly normal each subject who satisfies the conditions of steps (4) and (5).

16. A method according to claim 6, for testing whether a subject's ability to maintain an upright seated position in equilibrium by appropriately organizing sensory orientation inputs in the lateral plane of motion is normal with respect to direct sensory control criteria but grossly abnormal with respect to adaptive sensory control criteria, wherein step A of each of Test Procedures X, Y, and Z includes the further step of seating the subject on a support surface with the support surface rotation axis perpendicular to the line segment defined by the subject's hip joints at the center point of such segment, and wherein step B of Test Procedure X, step B of Test Procedure Y and step C of Test Procedure Z each include the further step of measuring the change in the angular orientation of the subject's trunk in the lateral plane around the support surface rotation axis, and wherein the method further comprises:

(4) Identifying as normal with respect to direct sensory control but grossly abnormal with respect to adaptive sensory control each subject who has maintained a position in equilibrium in Test X and Test Y but not in Test Z;

(5) Identifying as normal with respect to direct sensory control but grossly abnormal with respect to adaptive sensory control each subject who has maintained a position in equilibrium in Test X, Test Y, and Test Z but whose index of visually disinformed stability is at least approximately 1.5 times as great as his index of blind stability.

17. A method according to claim 6, for testing whether a subject's ability to maintain an upright seated position in equilibrium by appropriately organizing sensory orientation inputs in the lateral plane of motion is mildly abnormal with respect to either direct sensory control criteria or adpative sensory control criteria, wherein step A of each of Test Procedures X, Y, and Z includes the further step of seating the subject on a support surface with the support surface rotation axis perpendicular to the line segment defined by the subject's hip joints at the center point of such segment, and wherein step B of Test Procedure X, step B of Test Procedure Y and step C of Test Procedure Z each include the further step of measuring the change in the angular orientation of the subject's trunk in the lateral plane around the support surface rotation axis, and wherein the method further comprises:
- (4) identifying as mildly abnormal with respect to direct sensory control or with respect to adaptive sensory control each subject who maintains a position in equilibrium in step D of Test Procedure X, step D of Test Procedure Y and also step F of Test Procedure Z and whose index of blind stability and whose index of visually disinformed stability are each above the range of values for an age-matched normal population of subjects according to a statistical criterion of significance.

18. A method according to claim 6, for testing whether a subject's ability to maintain an upright seated position in equilibrium by appropriately organizing sensory orientation inputs in the lateral plane of motion is grossly normal, wherein step A of each of Test Procedures X, Y, and Z includes the further step of seating the subject on a support surface with the support surface rotation axis perpendicular to the line segment defined by the subject's hip joints at the center point of such segment, and wherein step B of Test Procedure Y and step C of Test Procedure Z each include the further step of measuring the change in the angular orientation of the subject's trunk in the lateral plane around the support surface rotation axis, and wherein the method further comprises:
- (4) Determining if the subject has maintained equilibrium in step D of each of Test Procedures X and Y and in step F of Test Procedure Z and also has an index of visually disinformed stability at least approximately 1.5 times as great as high index of blind stablity;
- (5) Determining if the subject has maintained equilibrium in step D of each of Test Procedures X and Y and in step F of Test Procedure Z and also has index of visually disinformed stability and an index of blind stability whose values are both above the range of values for an age-matched normal population of subjects according to a statistical criterion of significance;
- (6) Identifying as grossly normal each subject who satisfies the conditions of steps (4) and (5).

* * * * *